(12) United States Patent
Schnall

(10) Patent No.: US 7,374,540 B2
(45) Date of Patent: May 20, 2008

(54) NON-INVASIVE PROBE FOR DETECTING MEDICAL CONDITIONS

(75) Inventor: Robert P. Schnall, Kiryat Bialik (IL)

(73) Assignee: Itamar Medical Ltd., Caesarea (IL)

( * ) Notice: Subject to any disclaimer, the term of this patent is extended or adjusted under 35 U.S.C. 154(b) by 866 days.

(21) Appl. No.: 10/471,580

(22) PCT Filed: Mar. 26, 2002

(86) PCT No.: PCT/IL02/00249

§ 371 (c)(1),
(2), (4) Date: Sep. 12, 2003

(87) PCT Pub. No.: WO02/080752

PCT Pub. Date: Oct. 17, 2002

(65) Prior Publication Data

US 2004/0116787 A1    Jun. 17, 2004

Related U.S. Application Data

(60) Provisional application No. 60/281,388, filed on Apr. 5, 2001.

(51) Int. Cl.
*A61B 5/02* (2006.01)
*A61B 5/00* (2006.01)

(52) U.S. Cl. .................. 600/481; 600/500; 600/504; 600/323; 600/335; 600/310

(58) Field of Classification Search ............... 600/300, 600/301, 481, 483, 485, 488, 490–504, 506, 600/507, 322–324, 326, 328, 335, 344
See application file for complete search history.

(56) References Cited

U.S. PATENT DOCUMENTS

| | | | | |
|---|---|---|---|---|
| 2,438,901 A * | 4/1948 | Coxe | ................................. | 2/21 |
| 3,156,237 A * | 11/1964 | Edmark, Jr. | ................. | 600/496 |
| 3,482,565 A * | 12/1969 | Gowen | ........................ | 600/480 |
| 4,664,651 A * | 5/1987 | Weinshenker et al. | ....... | 604/115 |
| 4,862,895 A * | 9/1989 | Yamasawa et al. | .......... | 600/493 |
| 4,967,758 A * | 11/1990 | Masciarotte | ................. | 600/499 |
| 5,337,744 A * | 8/1994 | Branigan | ..................... | 600/407 |
| 5,452,717 A * | 9/1995 | Branigan et al. | ............ | 600/323 |
| 5,620,001 A * | 4/1997 | Byrd et al. | .................. | 606/202 |
| 5,669,390 A * | 9/1997 | McCormick et al. | ........ | 600/499 |
| 5,740,943 A * | 4/1998 | Shields et al. | ................. | 221/33 |
| 6,319,205 B1 * | 11/2001 | Goor et al. | .................. | 600/485 |
| 6,322,515 B1 * | 11/2001 | Goor et al. | .................. | 600/485 |
| 6,461,305 B1 * | 10/2002 | Schnall | ........................ | 600/485 |

(Continued)

*Primary Examiner*—Charles A. Marmor, II
*Assistant Examiner*—Navin Natnithithadha

(57) ABSTRACT

A non-invasive probe for application to a body part, such as a finger, toe or limb, for the detection of a medical condition of the subject includes a housing defining a compartment closed at one end and open at the opposite end for receiving the distal end of the subject's body part including its terminal-most extremity, a sensor for sensing a predetermined condition of the body part after being received within the compartment, and a removable liner lining the inner surface of the housing, to facilitate the insertion of the body part into the compartment. The described probe is one which senses changes in the peripheral arterial tone as manifested by changes in the pulsatile arterial blood volume and/or changes in the oxygen saturation level in a terminal extremity of a body part, and includes a number of other features particularly useful in such probes.

30 Claims, 11 Drawing Sheets

U.S. PATENT DOCUMENTS 6,478,745 B2 * 11/2002 Nakagawa et al. ......... 600/499
6,553,243 B2 * 4/2003 Gurley ....................... 600/340
6,916,289 B2 * 7/2005 Schnall ....................... 600/500
6,939,304 B2 * 9/2005 Schnall et al. .............. 600/481

* cited by examiner

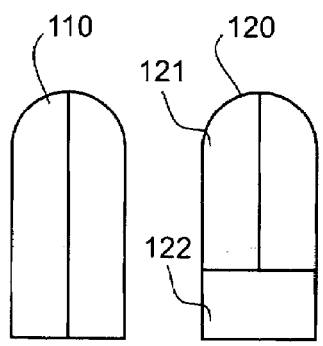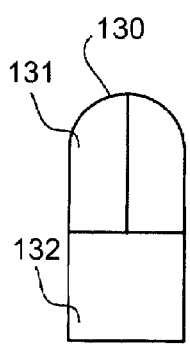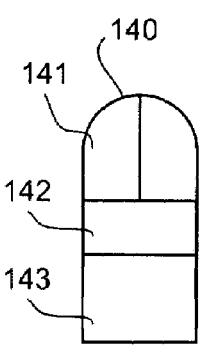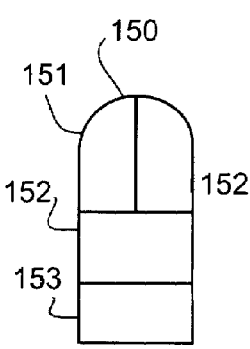
Fig. 7a  Fig. 7b  Fig. 7c  Fig. 7d  Fig. 7e
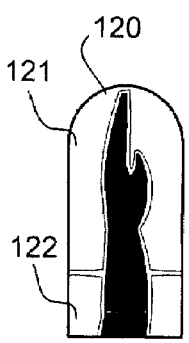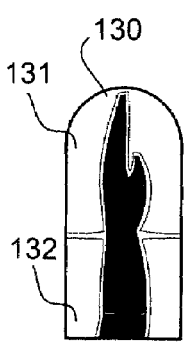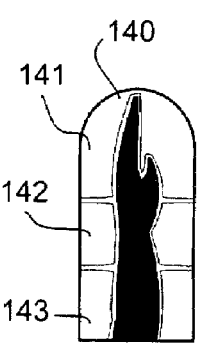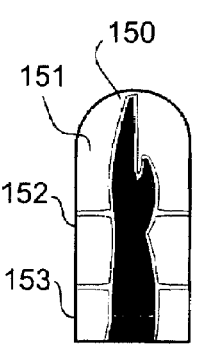
Fig. 8a  Fig. 8b  Fig. 8c  Fig. 8d  Fig. 8e

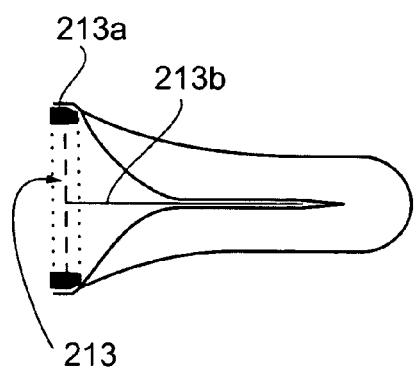
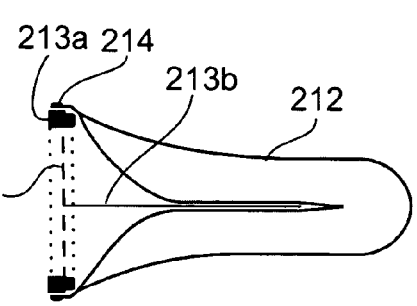
Fig. 11c    Fig. 11d    Fig. 11e
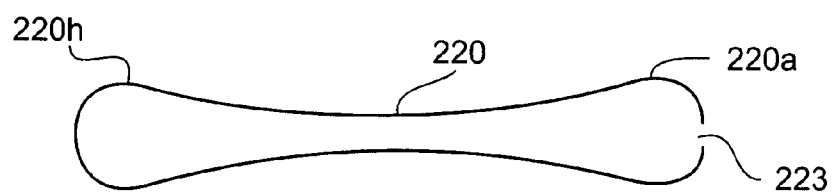
Fig. 12a
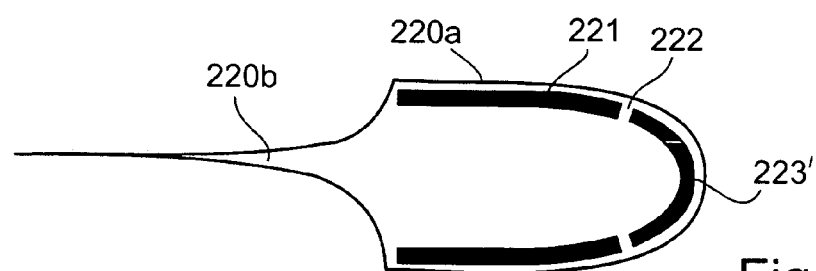
Fig. 12b

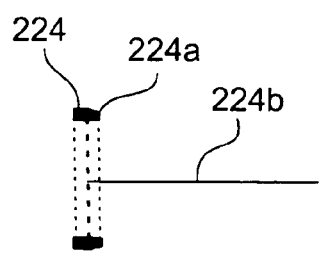
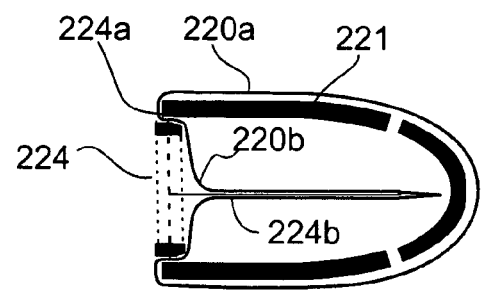
Fig. 12c    Fig. 12d
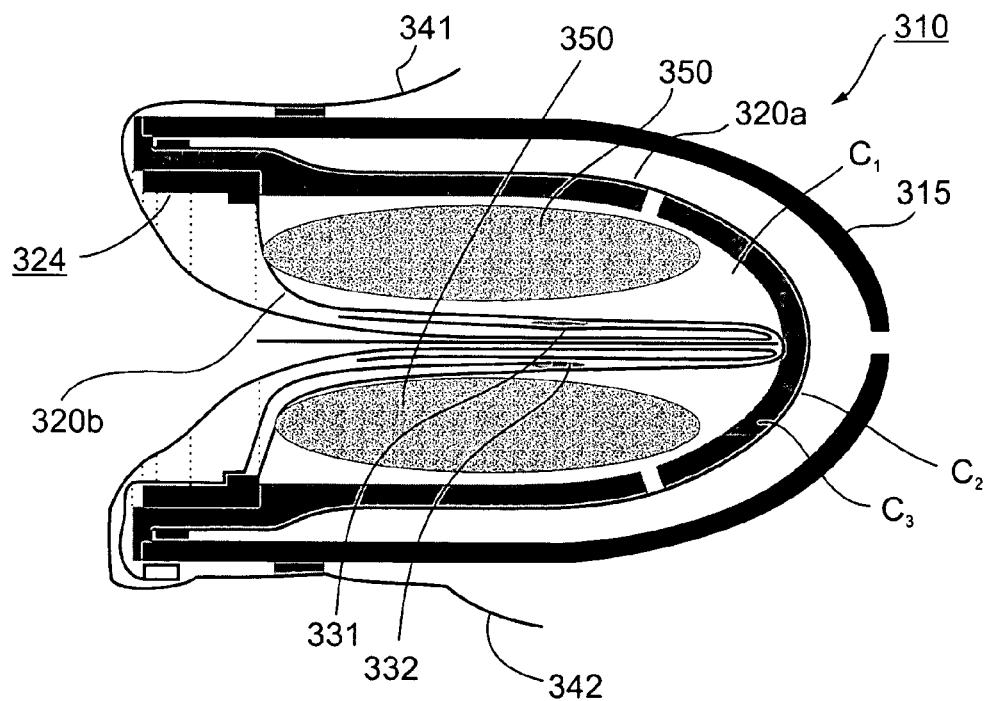
Fig. 13

NON-INVASIVE PROBE FOR DETECTING MEDICAL CONDITIONS

RELATED APPLICATIONS

The present application is a National Phase Application of PCT Application No. PCT/IL02/00249 having International Filing Dated Mar. 26, 2002 which claims priority from U.S. Provisional Patent Application No. 60/281,388, filed Apr. 5, 2001.

FIELD AND BACKGROUND OF THE INVENTION

The present invention relates to non-invasive probes for application to a body part of a subject for the detection of a medical condition of the subject. The invention is particularly useful in finger probes, such as described in U.S. Pat. Nos. 6,319,205 and 6,322,515, and in International Applications PCT/IL99/00292 (published Dec. 16, 1999 as International Publication No. WO 99/63884), PCT/IL00/00307 published Dec. 14, 2000 as International Publication No. WO 00/74551), PCT/IL00/00403 (published Jan. 18, 2001 as International Publication No. WO 01/03569; and PCT/IL01/00970, filed Oct. 22, 2001. The invention is therefore described below with respect to the probes described in the above patents and applications (hereinafter, "the above-identified U.S. patents and International Patent Applications"), but it will be appreciated that the invention could also be advantageously used in other types of probes.

The above-identified U.S. patents and International Patent Applications disclose various probe constructions, methods and apparatus for the non-invasive detection of a medical condition of a subject, particularly by monitoring changes in the peripheral arterial tone as manifested by changes in the pulsatile arterial blood volume in a terminal extremity of a body part, e.g., a digit (finger or toe) of the subject. The various medical conditions detected by such probes, as described therein, include mycardial ischemia, sleep apnea, endothelial dysfunction (ED), sleep disorders, mental stress, sympathetic nervous system reactivity, blood pressure, etc.

In general, the probes described in the above-identified U.S. patents and International Applications include a housing defining a compartment closed at one end and open at the opposite end for receiving the distal end of the subject's body part, such as a finger or toe, including its terminal-most extremity, and a sensor for sensing a predetermined condition of the body part after being received within the compartment. The preferred embodiments described therein are particularly useful for monitoring peripheral arterial tone in a subject's finger, and for this purpose, they include pressurizing means for applying a static pressure field substantially uniformly around the distal end of the subject's finger, including its terminal-most extremity. The pressure field is of a predetermined magnitude sufficient to substantially prevent distention of the venous vasculature, uncontrolled venous backflow and retrogade shockwave propagation into the distal end of the finger, and to partially unload the wall tension of, but not to occlude, the arteries in the distal end of the finger when at heart level or below. The probe sensor senses changes in the distal end of the subject's finger (or other body part) related to changes in volume therein due to pulsatile changes in instantaneous blood volume related to arterial tone.

Further particulars as to the construction of such probes, and the various medical conditions for which they may be used, are available in the above-identified U.S. patents and International Patent Applications, the contents of which are hereby incorporated by reference herein.

Because of the potential diagnostic capabilities of such probes, considerable research and development has been conducted to improve their construction, to make them more convenient to use, and to extend their diagnostic range.

BRIEF SUMMARY OF THE PRESENT INVENTION

The present invention relates to a number of improvements in non-invasive probes in general, which improvements are particularly useful in the probes described in the above-identified U.S. patents and International Applications, and which produce a number of advantages when implemented in such probes as will be more particularly described below.

According to one aspect of the present invention, there is provided a non-invasive probe for application to a body part of the subject for the detection of a medical condition of the subject, comprising: a housing defining a compartment closed at one end and open at the opposite end for receiving the subject's body part; a sensor for sensing a predetermined condition of the body part after being received within the compartment; and two removable liners of a low-friction sheet material lining two inner surfaces of the housing to face opposite sides of the body part when received in the compartment, each of the liners including an internal portion located within the housing, and an external portion extending externally of the housing to facilitate the slidable withdrawal of each liner from the housing after the body part has been inserted into the compartment.

According to another aspect of the present invention, there is provided a probe for application to a body part of a subject for the non-invasive detection of a medical condition of the subject, comprising: a housing defining a compartment closed at one end and open at the opposite end for receiving the distal end of the subject's body part including its terminal-most extremity; and a sensor for sensing a predetermined condition of the body part after being received within the compartment; the housing including: an inner casing; an inner membrane within the casing and defining an inner chamber for receiving a fluid to apply a predetermined static pressure to the body part when received within the compartment; an outer membrane over the outer surface of the inner casing and defining therewith an outer chamber communicating with the inner chamber via an opening in the inner casing effective to cause said predetermined static pressure applied by the inner membrane to be substantially unaffected by the size of the body part inserted into said compartment or by volume changes of the body part inserted therein; and an outer casing facing the outer surface of the outer membrane and defining therewith a third chamber; the outer casing including a vent opening venting the third chamber to the atmosphere.

According to further features in a described preferred embodiment, the probe further includes a pressure transducer for monitoring pressure changes within the third chamber via an opening in the outer casing.

According to yet another aspect of the present invention, there is provided a probe for application to a body part of a subject for the non-invasive detection of a medical condition of the subject, comprising: a housing defining a compartment closed at one end and open at the opposite end for receiving a distal end of the subject's body part including its terminal-most extremity; the housing including a casing, and an inner membrane within the casing defining, with the inner surface of the casing, a chamber for receiving a fluid to apply a predetermined static pressure to the body part when received within the compartment; a restraining member within the compartment to restrain the membrane from expelling the body part from the chamber when the chamber is pressurized by the static pressure; and a sensor for sensing a predetermined condition of the body part after being received within the compartment; the restraining member including an annular ring adjacent to the open end of the housing, and a plurality of arms extending axially within the compartment and terminating short of the closed end of the housing, and thereby short of the terminal-most extremity of the body part when received within the compartment.

According to further features in a described preferred embodiment, the sensor is an optical sensor including a light source and a light detector located externally of the compartment, and the arms of the restraining member include a light guide for guiding light into the interior of the compartment from the light source externally of the compartment, and for guiding light from the interior of the compartment to the light detector located externally of the compartment.

According to yet another aspect of the present invention, there is provided a probe for application to a body part of a subject for the non-invasive detection of a medical condition of the subject, comprising: a housing defining a compartment closed at one end and open at the opposite end for receiving a distal end of the subject's body part including its terminal-most extremity; the housing including a casing and a membrane within the casing and defining a chamber for receiving a fluid to apply a predetermined static pressure to the body part when received within the compartment; a restraining member within the compartment to restrain the membrane from expelling the body part from the chamber when the chamber is pressurized by the static pressure; and a sensor for sensing a predetermined condition of the body part after received within the compartment; the membrane being part of an inflatable elastic bag located within the housing and engaged by the restraining member to define the compartment after receiving the body part of the subject; the casing including an opening for venting the space between the elastic bag and the inner face of the casing.

According to a still further aspect of the present invention, there is provided a probe for application to a body part of a subject for the non-invasive detection of a medical condition of the subject, comprising: a housing defining a compartment closed at one end and open at the opposite end for receiving a distal end of the subject's body part including its terminal-most extremity; the housing including a casing, an inner membrane within the casing and defining an inner chamber for receiving a fluid to apply a predetermined static pressure to the body part when received within the compartment, and an outer membrane defining an outer chamber communicating with the inner chamber via an opening through the casing effective to cause the predetermined static pressure applied by the inner membrane to be substantially unaffected by the size of the body part inserted into the compartment or by volume changes of the body part inserted therein; a restraining member within the compartment to restrain the inner membrane from expelling the body part from the inner chamber when the inner chamber is pressurized by the static pressure; and a sensor for sensing a predetermined condition of the body part after received within the compartment; the restraining member including an annular ring facing the open end of the housing, and a plurality of arms extending axially within the compartment; the annular ring being located inwardly of the open end of the housing to define, with an inner section of the inner membrane, an inner section of the compartment for receiving the body part; the inner membrane including an outer section defining an outer section of the compartment for receiving the body part, and an outer section of the inner chamber for applying the static pressure to the body part when received in the compartment.

As will be described more particularly below, this feature provides a number of advantages, including a reduction in the tendency for the body part (e.g., finger) to be partially expelled from the probe.

According to a still further aspect of the present invention, there is provided a probe for application to a body part of a subject for the non-invasive detection of a medical condition of the subject, comprising: a housing defining a compartment closed at one end and open at the opposite end for receiving a distal end of the subject's body part including its terminal-most extremity; and a sensor for sensing a predetermined condition of the body part after being received within the compartment; the housing including: an inner casing; an inner membrane within the inner casing and defining an inner chamber for receiving a fluid to apply a predetermined static pressure to the body part when received within the compartment; an outer membrane over the outer surface of the inner casing and defining herewith an outer chamber communicating with the inner chamber via an opening in the inner casing; and a retraining member within the compartment; the inner and outer membranes being parts of an inflatable elongated elastic bag; one end of the elongated elastic bag being received over the outer surface of the casing to constitute the outer membrane defining the outer chamber; the opposite end of the elongated elastic bag being received within the casing to constitute the inner membrane engageable by the restraining member and defining the inner chamber communicating with the outer chamber via an opening in the casing.

According to further features in the described preferred embodiments of this aspect of the invention, the casing and the elongated elastic bag are so dimensioned that the one end of the elongated elastic bag, when received over the casing to define the outer chamber, is pre-tensioned sufficient to reduce diffusion of the fluid through the wall of the bag by reducing the static pressure when the body part is not received within the compartment, but not to substantially affect the deform ability of the inner membrane by pulsatile volume changes in the body part when received in the compartment.

In one described preferred embodiment, the inner chamber is partially filled with a supporting medium, and is at a fluid pressure below the predetermined static pressure, such that the added volume of the distal end of the subject's body part, when received within the compartment, produces the predetermined static pressure applied to the body part. As one example, the supporting medium may be or include a spongy body.

In another described preferred embodiment, the probe includes a pair of bistable elastic spring leaves carried by the casing and disposed within the inner chamber on opposite sides thereof; each of the bistable elastic spring leaves being movable to a first stable position projecting away from the casing inner surface into the inner chamber for pre-tensioning the membranes to reduce diffusion of the fluid through the membranes by the fluid pressure within the elongated elastic bag; each of the bistable elastic spring leaves being movable to a second stable position in contact with the casing inner surface to accommodate the subject's body part when introduced into the compartment.

According to a still further aspect of the present invention, there is provided a probe for the non-invasive detection of a medical condition of a subject, comprising: a housing defining a compartment closed at one end and open at the opposite end for receiving a limb of the subject including the distal end of the limb; an inner membrane within the housing and defining an inner chamber for receiving a fluid to apply a predetermined static pressure to the limb including the distal end thereof within the compartment; a restraining member within the compartment; and a sensor within the compartment for sensing a predetermined condition of the distal end of the limb within the compartment.

According to one described embodiment, the predetermined static pressure is produced by fluid self-contained within the probe, and in another described embodiment, it is produced by a fluid supplied from a fluid system external to the probe.

According to further features in this aspect of the invention, the compartment defined by the housing, and the inner chamber defined by the inner membrane, are divided into a plurality of sections, including a distal section at the closed end of the compartment for receiving the distal end of the limb, and at least one proximal section of the opposite open end of the compartment for receiving one or more proximal regions of the limb; the distal section and/or proximal sections of the compartment being subjected to the predetermined static pressure and including the sensor or sensors for sensing the predetermined condition of the distal end of the limb.

The proximal section and the distal section, or any of the intervening sections, of the compartment are also subjected to a predetermined static pressure, and any of such sections may incude sensing means for sensing the predetermined condition of the limb in the respective section of the compartment.

As described more particularly below, such a probe may be used to induce ischemia in a patient for evaluating the degree of induced reactive hyperemia for the purpose of determining the endothelial function state of the patient. The ischemia may be induced by applying pressure to at least one of the plurality of sections of the compartment by a fluid supplied from a fluid system external of the probe and of sufficient magnitude to occlude the flow of blood, the measurements of pulsatile volume changes taken during the application of counter-pressure for occluding blood flow being used to ensure that a sufficient level of counter-pressure is being applied to completely occlude the flow of blood.

As will be described more particularly below, the foregoing features, when applied to probes constructed in accordance with above-identified U.S. patents and International Patent Applications, significantly improve the operation of the probe, greatly facilitate its use, and extend its diagnostic capabilities.

Further features and advantages of the invention will be apparent from the description below.

BRIEF DESCRIPTION OF THE DRAWINGS

The invention is herein described, by way of example only, with reference to the accompanying drawings, wherein:

FIGS. 7a-7e schematically illustrate various basic constructions of large-scale probes in accordance with the present invention for receiving a limb or part of a limb (e.g., a forearm) of the subject, rather than a finger or toe;

FIGS. 8a-8e schematically illustrate the large-scale probes of FIGS. 7a-7e, respectively, with a subject's forearm received therein;

FIG. 11 schematically illustrates another probe constructed with an elastic bag filled with a fluid to define the inner chamber which detects the pulsatile blood volume changes in the examined finger; while FIG. 11c illustrates the elastic bag retained in its folded condition by the restraining member; FIG. 11d illustrates a clamping ring for clamping the ends of the elastic bag between it and the annular ring of the restraining member; and FIG. 11e illustrates the assembly of the folded elastic bag with its ends clamped between the annular ring of the restraining member and the clamping ring of FIG. 11d;

FIGS. 12a-12d schematically illustrate another probe constructed in accordance with the present invention utilizing an inflatable bag and a rigid shell for supporting the membrane in an expanded manner to minimize diffusion of the fluid through the membrane when the subject's finger (or other body part) is not received within the compartment, FIG. 12a illustrating the inflatable bag, FIG. 12b illustrating the rigid shell to receive the inflatable bag, FIG. 12c illustrating the restraining member, and FIG. 12d illustrating the assembly of the bag, shell and restraining member;

FIG. 13 is a longitudinal sectional view schematically illustrating another probe constructed in accordance with the present invention and including sponge inserts for supporting the membrane in an expanded manner to minimize diffusion of the fluid through the membrane when the probe is not in use; FIGS. 14a, 15a being side and end views, respectively, illustrating one stable state of the bistable member when the probe is not in use; FIGS. 14b, 15b being corresponding views illustrating the second stable state of the bistable member when the subject's finger is inserted; and FIGS. 14c, 15c being corresponding views as FIGS. 14b, 15b but illustrating the second stable state with the finger withdrawn.

DESCRIPTION OF PREFERRED EMBODIMENTS

Figure 1:
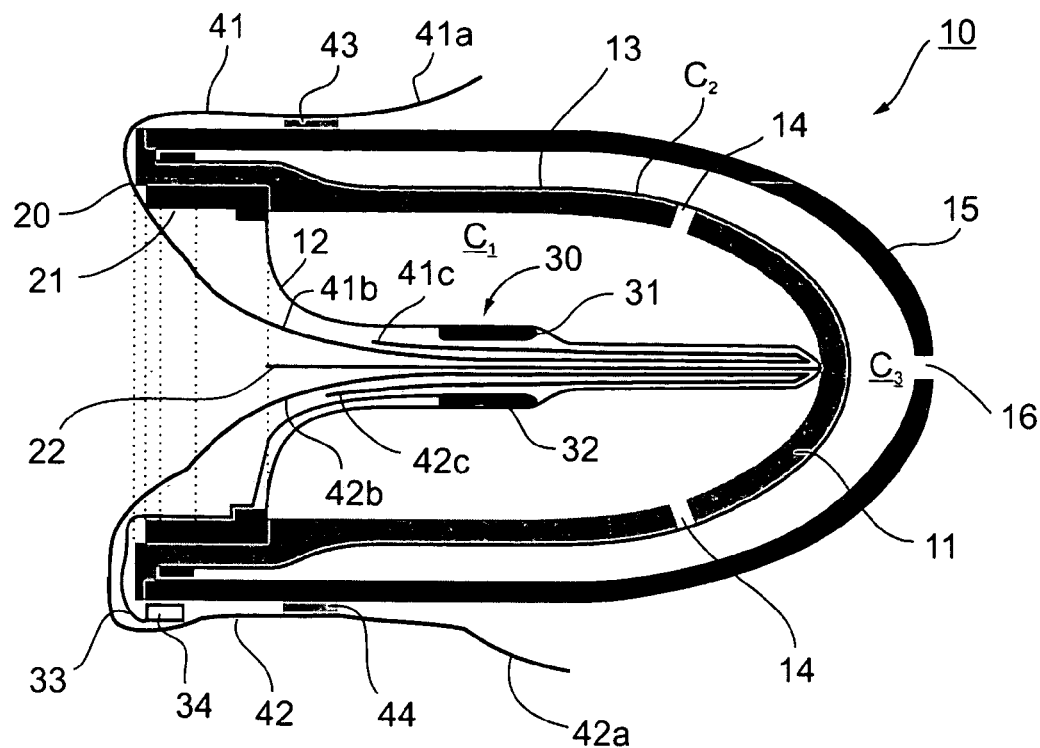
FIG. 1 is a cross-sectional view schematically illustrating one form of finger probe constructed in accordance with the present invention.

FIG. 1 illustrates a probe, therein generally designated 10, of a construction similar to that described in the above-identified U.S. patents and International Patent Applications for receiving the distal end of a subject's finger, including its terminal-most extremity, and for detecting one or more medical conditions of the subject by monitoring pulsatile blood volume changes in the finger. Briefly, probe 10 includes a housing containing an inner casing 11 of thimble shape to define a compartment closed at one end and open at the opposite end for receiving a subject's finger. Probe 10 further includes a first, inner membrane 12 defining, with the inner surface of casing 11, an inner chamber $C_1$ for receiving a fluid to apply a static pressure to the subject's finger when received within the compartment, and a second membrane 13 defining a second chamber $C_2$ communicating with the first chamber $C_1$ via openings 14 through casing 11.

As distinguished from the probe constructions described in the above-identified U.S. patents and International Patent Applications, probe 10 further includes an outer casing 15 defining a third chamber $C_3$ with the second membrane 13. This third chamber $C_3$ is vented to the atmosphere via an opening 16 formed in the outer casing 15. The provision of the outer casing 15, together with its vent opening 16, provides a number of important advantages as will be described more particularly below.

Probe 10 further includes a restraining member, generally designated 20, which is located within the compartment defined by casing 11 and membrane 12 for receiving the subject's finger. As described in the above-identified U.S. patents and International Patent Applications, restraining member 20 restrains the inner membrane 12 from expelling the subject's finger from the compartment when chamber $C_1$ is pressurized. Restraining member 20 may be of the construction as described in the above-cited patents and applications, to include an annular ring 21 at the open end of the probe 10 and mounting a U-shaped bar 22 extending to the closed end of the compartment defined by the inner membrane 12 and inner casing 11, as described in those patents and applications. Preferably, however, the restraining member 20 is of the construction described below with respect to FIGS. 5 and 6, which construction provides a number of advantages also to be described below.

Probe 10 further includes an optical sensor 30 for sensing changes in the optical characteristics of the finger inserted within the compartment of the probe. In this case, the optical sensor 30 senses the density of the light passing through the skin of the subject's finger inserted within the compartment, and therefore includes a light source 31 and a light detector 32 staggered up to 180° with respect to each other. In FIG. 1 they are shown as located on the opposite sides of the compartment such that the detector 32 is displaced 180° with respect to the light source 31. The light source 31 and detector 32 are externally connected to a measuring system by electrical leads 33 and a connector 34.

Except for the provision of the outer casing 15, probe 10 illustrated in FIG. 1 is constructed and used in the manner described in the above-cited U.S. patents and International Patent Applications, and therefore further details of the construction and use of such a probe are not set forth herein.

In accordance with one aspect of the present invention, probe 10 illustrated in FIG. 1 is provided with a removable liner lining the inner surface of the compartment receiving the subject's finger. This liner is of a low-friction sheet material to facilitate the insertion of the subject's finger into the compartment. Such a liner is particularly useful in probes having a self-contained fluid for producing the predetermined static pressure applied to the finger and facilitates the insertion of the subject's finger and provides a low-friction surface between the finger and the inner membrane 12 under the static pressure. The low-friction property of the liner, together with the manner in which it is disposed between the subject's finger and the inner membrane 12, also facilitates the slidable withdrawal of the liner from between the subject's finger and the inner membrane.

As shown in FIG. 1, probe 10 actually includes two liners, 41 and 42, for lining the two inner surfaces of the housing compartment to face the opposite sides of the subject's finger when inserted therein. Each of the liners 41, 42 includes an external portion, as shown at 41a and 42a, respectively, extending externally of the outer casing 15, and an inner portion including two (or more) folded sections 41b, 41c and 42b, 42c, respectively, received within the compartment between the inner membrane 12 and the subject's finger when inserted into the compartment.

As shown in FIG. 1, the externally-extending portions 41a, 42a of the liner sheets are temporarily adherent to the outer surface of the outer casing 15. This may be done by the provision of spots of adhesive 43, 44, between the respective liner and the outer casing.

Figure 2A:
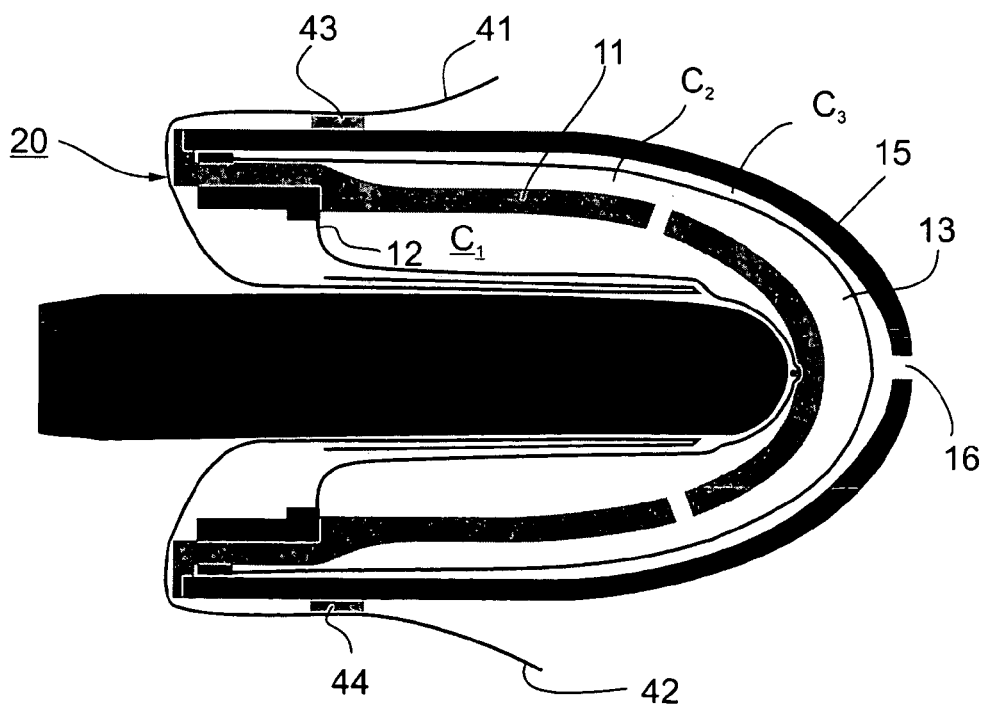
FIGS. 2a-2c illustrate three stages in the use of the finger probe of FIG. 1.
Figure 2B:
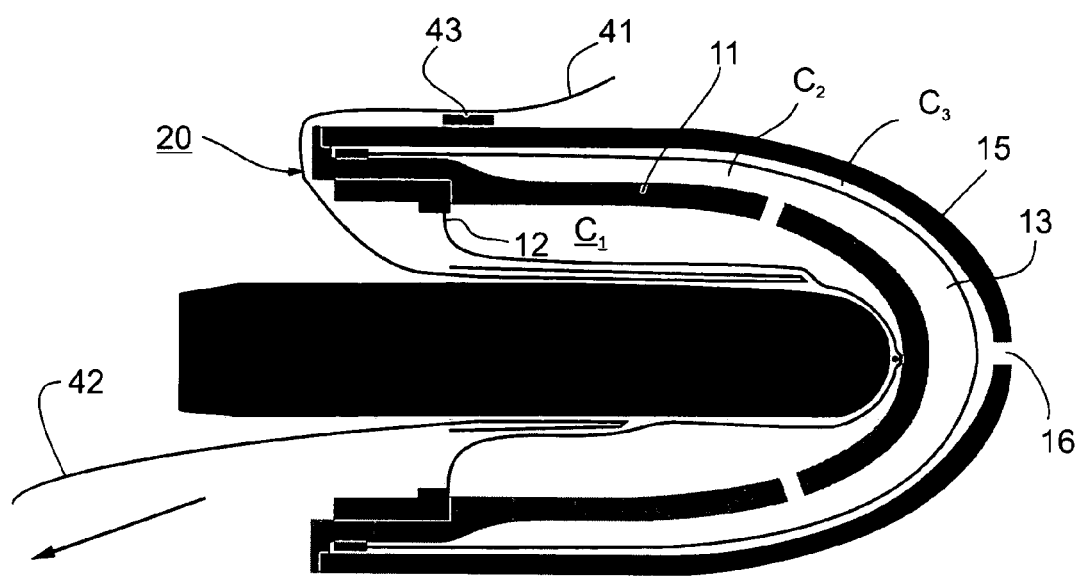
Figure 2C:
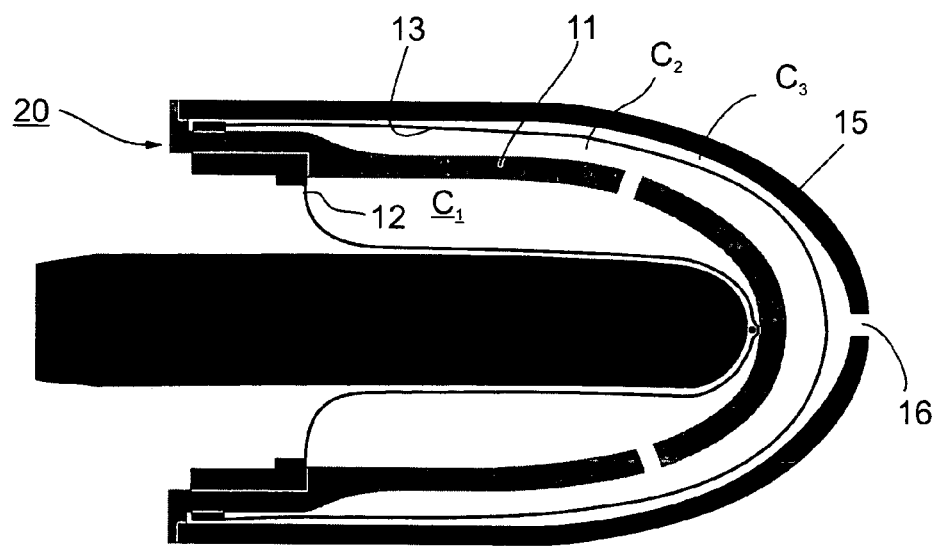

FIG. 2a illustrates the probe 10 of FIG. 1 after the subject's finger has been inserted into the probe compartment, which insertion is facilitated by the provision of the liner sheets 41, 42, as described earlier. FIG. 2b illustrates the condition as one of the liner sheets 42 is being withdrawn by grasping its external portion 42a, and pulling it outwardly to first release it from its adherence at 44 to the outer casing 15, and then to start its slidable withdrawal from the probe compartment. FIG. 2c illustrates the condition of the probe after liner 42 has been fully withdrawn, and the other liner 41 has also been withdrawn in the same manner. Providing the internal portion of each liner with the folded sections 41b, 41c and 42b, 42c, as illustrated in FIG. 1, facilitates the slidable withdrawal of each liner.

Figure 3:
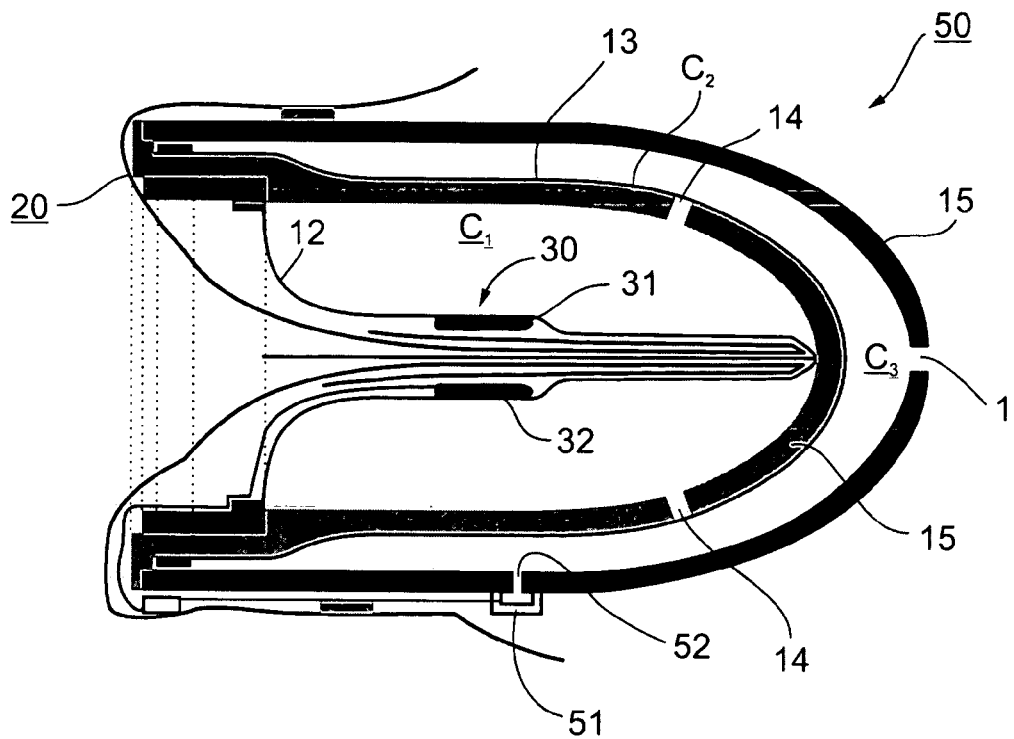
FIG. 3 is a cross-sectional view schematically illustrating another finger probe constructed in accordance with the present invention.

Including the outer casing 15 in probe 10 illustrated in FIG. 1 produces a number of advantages. Thus, the outer casing 15 provides a rigid surface for adhering the removable liner strips 41, 42, e.g., at the adhesion points 43, 44. In addition, since the outer casing 15 encloses the outer membrane 13, it provides protection for that membrane, both during the use of the probe, and also during its handling and storage before use and between uses FIG. 3 illustrates a further advantage that may be provided by the outer casing 15, in that it enables pulsatile changes in the finger blood volume to be measured simultaneously with changes in the optical density. For this purpose, the probe illustrated in FIG. 3, therein designated 50, is provided with a pressure transducer 51, communicating, via an opening 52 in the outer casing 15, with chamber $C_3$ between the outer casing 15 and the outer membrane 13. In this case, vent opening 16 in the outer casing 15 is of relatively small diameter, as shown at 16', so as to retard the equalization of the air pressure within chamber $C_3$ to atmospheric pressure. This enables transducer 50 to measure the slight pressure swings developed in the probe due to the pulsatile blood volume changes in the finger of the subject received within the probe. It will be appreciated that signals developed by transducer 50 correspond to the pulsatile blood volume changes in the finger and are derived from the probe itself, i.e., without any connection to an external fluid system.

Probe 50 illustrated in FIG. 3 is otherwise constructed as probe 10 described above with respect to FIG. 1, and includes the optical sensor 30, constituted of light source 31 on one side of the finger and light detector 32 on the opposite side, for measuring changes in the optical density of the finger resulting from pulsatile blood volume changes in the finger.

It will be appreciated that probe 10 illustrated in FIG. 1 and/or probe 50 illustrated in FIG. 3, as well as the other probes described below, may be used to measure, not only pulsatile volume changes, but also other changes, e.g., oxygen saturation level, blood pressure, etc., together with, or in lieu of, changes in the pulsatile blood flow through the finger received in the probe, as described in any of the above-identified U.S. patents and International Patent Applications. For example, such probes may include, in addition to the optical sensors or in lieu thereof, Hall Effect or other flow-related electromagnetic sensors, electrical impedance sensors, strain gauge sensors, Doppler sensors, isotope washout sensors, thermal washout sensors, etc. related to changes in the pulsatile blood flow through the finger.

Figure 4:
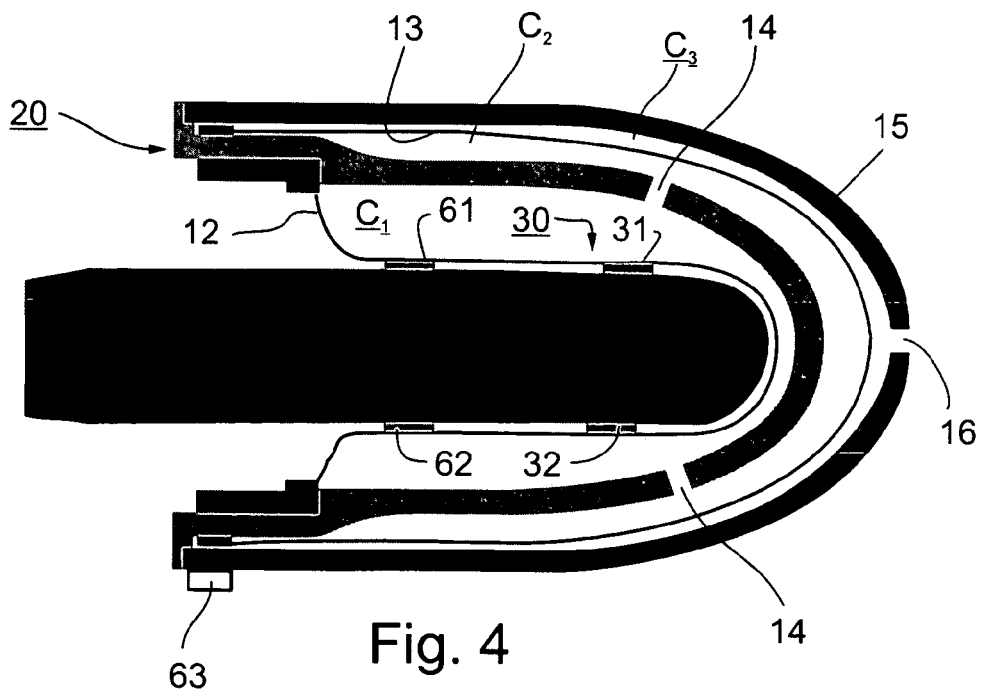
FIG. 4 schematically illustrates the probe of FIG. 3 after a subject's finger has been inserted into the probe and illustrates the addition of further sensing modalities.

FIG. 4 illustrates a probe 60, such as described above with respect to FIG. 1, including the above-described optical sensor 30, but including a second optical sensor for sensing the optical density of the examined finger at two different locations of the finger. Thus, optical sensor 30 including light source 31 and light detector 32, monitors changes in the optical density of the palmar region of the finger; whereas the second optical sensor, including light source 61 and light detector 62, monitors changes in the dorsal region of the finger. By thus deriving optical density changes (and other volume-related changes if desired) from histologically different cutaneous regions, probe 60 can monitor changes in the vascular beds serving predominantly nutritive roles separate and apart from those serving predominantly thermoregulatory roles. Signals derived from each of these sites, and their relationship to each other based on concurrent recordings, may provide further information regarding the responses of the vascular beds to the monitored changes in the physiological state of the subject.

The illustrated probe may be further modified by incorporating into the probe a patient movement detecting device, such as an actigraph. FIG. 4 illustrates probe 60 with the addition of such a device, at 63, attached to the outer surface of the outer casing 16. It will be appreciated, however, that a movement detecting device could also be included on a wrist-mounted unit, or on a unit mounted on a different part of the subject's body, connected to the finger probe.

Figure 5A:
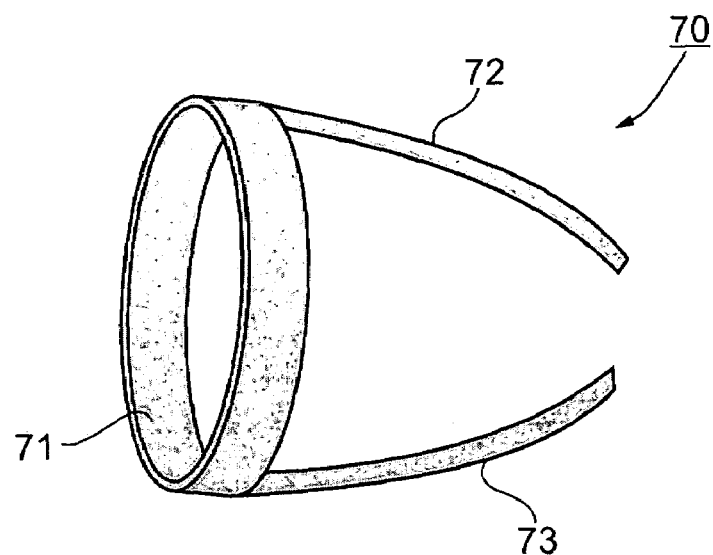
FIG. 5a schematically illustrates one form of restraining member constructed in accordance with another aspect of the present invention to be located within the finger probe in order to restrain the membrane therein from expelling the finger when the chamber is pressurized.
Figure 5B:
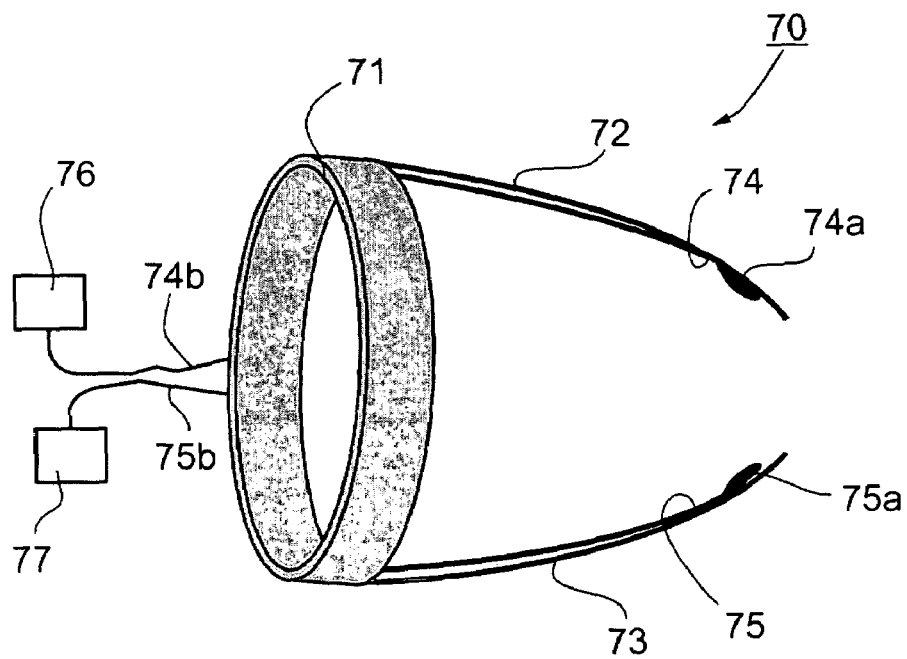
FIG. 5b illustrates the restraining member of FIG. 5a also used for mounting light guides for enabling the optical sensor to be mounted externally of the probe.

FIGS. 5a and 5b illustrate a modification in the design of the restrainer member (20, FIG. 1) that may be included in the improved probe construction. As indicated earlier, the purpose of the restraining member is to restrain the membrane (12, FIG. 1) from expelling the subject's finger from the probe compartment when chamber $C_1$ is pressurized. In the above-identified U.S. patents and International Patent Applications (and also in FIG. 1 of the present application), the restraining member 20 includes an annular ring to be located adjacent to the open end of the housing, and a U-shaped bar to extend towards the closed end of the housing.

In the modified construction of the restraining member shown in FIG. 5, and therein generally designated 70, the restraining member also includes an annular ring 71 to be located adjacent to the open end of the housing. However, instead of a U-shaped member, it includes a pair of arms 72, 73 to extend axially towards the closed end of the housing but terminating short of the closed end, and thereby short of the terminal-most extremity of the subject's finger when received in the probe compartment. Thus, the restraining member 70 illustrated in FIG. 5 is similar to restraining member 20 described above with respect to FIG. 1, except that the bend at the end of the U-shaped bar 22 is removed, thereby effectively creating the two arms 72, 73 which are disconnected at their ends.

Such a construction as illustrated in FIG. 5 makes the arms 72, 73 more flexible than the U-shaped bar (22 in FIG. 1), thereby enabling their free ends to better accommodate the outer contour of the finger received within the probe compartment. This in turn better allows the static pressure field within the inner chamber $C_1$ to be more uniformly applied around the complete surface of the finger introduced within the probe compartment.

Arms 72, 73 may be of the same length as the U-shaped bar 22 in the FIG. 1 construction. Preferably, however, they are slightly shorter so as to terminate short of the terminal-most extremity of the finger inserted into the probe. In addition, arms 72, 73 may be of any suitable elastic material, metal or plastic, enabling them to conform to the shape of the underlying surface of the finger, and allowing for a more uniform pressure field to be applied to the finger. Alternatively, there may be more than two arms, of the same lengths or of different lengths, and aligned with each other or staggered with respect to each other so that they do not directly overlap.

The restraining member 70 shown in FIG. 5a may also be used for mounting the optical or other sensors used within the probe. This is shown in FIG. 5b, wherein the two arms 72, 73 of the restraining member 70 mount the distal ends of a pair of optical fibers 74, 75, while the proximal ends of the optical fibers 74, 75, are mounted on the annular ring 71 of the restrainer member 70. Thus, the distal ends 74a, 75a, of the optical fibers 74, 75 are disposed within the probe to detect optically-sensitive changes in the subject's finger inserted therein, whereas the proximal ends 74b, 75b of the optical fibers are disposed externally of the probe to communicate with a light source 76 and a light detector 77, respectively, externally of the probe.

Optical fibers 74, 75 mounted on restraining member 70 in the probe illustrated in FIG. 5b may thus be used for guiding light into the interior of the probe compartment from light source 76 externally of the compartment, and for guiding light from the interior of the compartment to light detector 77 externally of the compartment for measuring changes in the optical density of the examined finger due to pulsatile blood volume changes, and/or oxygen saturation level changes. Such an arrangement provides a number of advantages. It eliminates the need for having the light source and the light detector located within the probe compartment, thereby avoiding local heating of the finger by the heat of the light source since the light source would be situated remotely from the skin surface being illuminated. In addition, such an arrangement permits a more compact construction for the probe since the electronic elements would not be part of the probe itself.

It will be appreciated that the two arms 72, 73 of the restraining member 70 may be constructed of the light-conducting material so as to serve both the restraining function and the light guiding function. It will also be appreciated that the arms 72, 73 of the restraining member 70 can be used for mounting other types of sensors within the probe including their connections to external devices.

Figure 6:
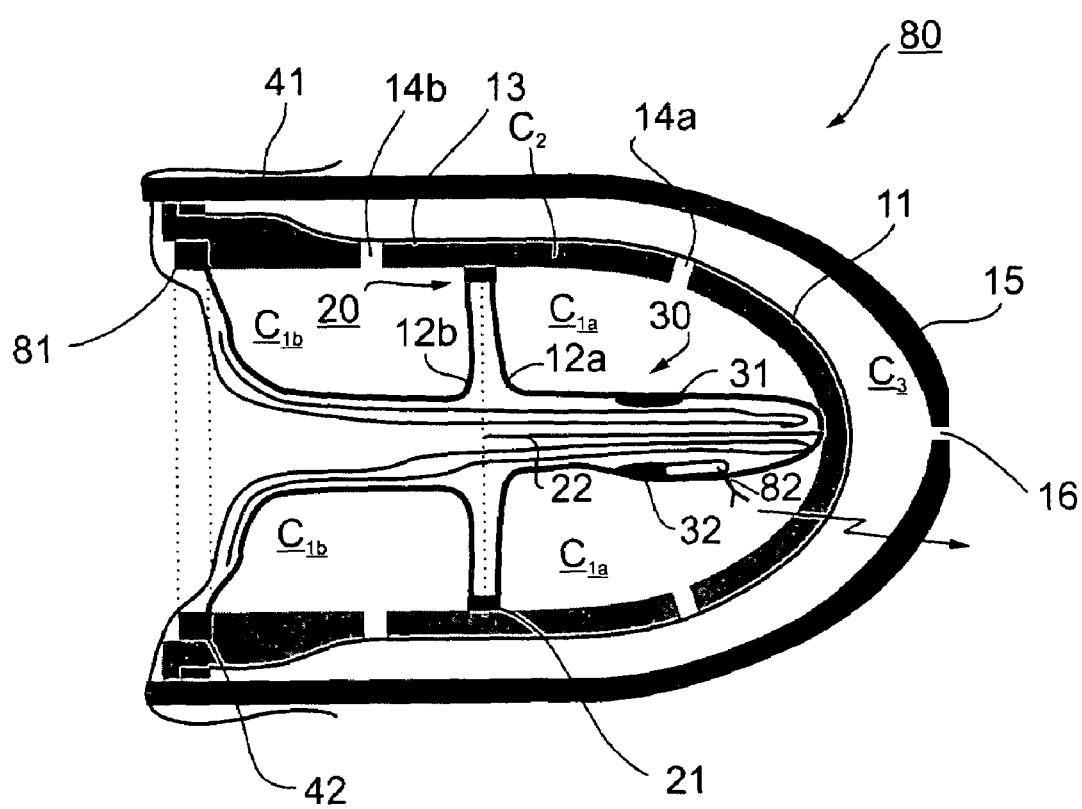
FIG. 6 is a view similar to that of FIG. 1 but illustrating a probe having a two-section compartment for receiving the subject's finger.

FIG. 6 illustrates a probe constructed similarly to that of FIGS. 1 and 3 but modified such that the compartment for receiving the subject's finger (or other body part) is divided into inner and outer sections, with the restraining member applied only in the inner section of the probe. For purposes of brevity and facilitating understanding, those elements of the probe illustrated in FIG. 6 which are generally similar to those in FIG. 1 are identified by the same reference numerals.

Thus, the probe illustrated in FIG. 6, and therein generally designated 80, is of a similar construction as in FIG. 1, except the restraining member 20 is spaced inwardly of the compartment so as to define an inner section of the compartment for receiving the terminal-most part of the subject's finger. Annular ring 21 of restraining member 20 is located inwardly of the open end of the housing such that its pair of arms 22 define, with an inner section 12a of the inner membrane 12, an inner section of the compartment for receiving the terminal-most part of the subject's finger, and inner section $C_{1a}$ of the inner chamber $C_1$ for applying the static pressure to the terminal-most part of the subject's finger. The probe further includes another annular ring 81 which engages the outer end of the inner membrane 12 to define an outer section $C_{1b}$ of the inner chamber $C_1$ with the outer section $12_b$ of the inner membrane 12. The outer section 12b of the inner membrane 12 thus defines an outer section of the compartment receiving the subject's finger, and an outer section $C_{1b}$ of the inner chamber for applying the static pressure field to the remainder of the subject's finger receiving within the probe.

As also seen in FIG. 6, the inner casing 11 of the probe is formed with vent openings 14a venting section $C_{1a}$ of the inner chamber $C_1$ to the outer chamber $C_2$, and separate venting openings 14b for venting the outer section $C_{1b}$ of the inner chamber $C_1$ to the outer chamber $C_2$. In all other respects, the probe illustrated in FIG. 6 is otherwise constructed and operates in the same manner as described above.

An important advantage of the construction illustrated in FIG. 6 is that such a construction decreases any tendency of the finger from being expelled from the probe by the pressure within the inner chamber C1 applied to the finger when the two liner 41, 42 are withdrawn. Thus, as the two liners are withdrawn, the inner section 12a of the inner membrane 12 comes into direct contact with the terminal-most part of the subject's finger to better hold the finger within the probe as the respective liner is withdrawn from between the outermost part of the subject's finger and the outer section 12b of the inner membrane 12.

It will be appreciated that the restraining member 20 illustrated in FIG. 6 could be of either the U-bend construction or of the free-end construction illustrated in FIGS. 5a and 5b, and that the arms could also be used for mounting the sensor 30 and its connections to locations externally of the probe.

FIG. 6 illustrates a further feature that may be included in the probe of FIG. 6, or in any of the other described probes, namely the provision of a transmitter 82 mounted for example on one of the arms of the restraining member 20 as shown in FIG. 6, or at the terminal end of the connecting wiring as shown in FIG. 1 by connector 34, for transmitting, in a wireless manner, data sensed by the sensor 30 to a receiver (not shown) externally of the compartment receiving the subject's finger.

FIGS. 7a-7e schematically illustrate a number of probe constructions for application to other body parts of the subject, in particular to a limb of the subject, for detecting a medical condition in accordance with the method of any of the above-identified U.S. patents and International Patent Applications. The probes schematically illustrated in FIGS. 7a-7e are constructed and dimensioned for application to an arm of the subject, as shown in FIGS. 8a-8e, respectively, including the terminal-most extremities of the fingers of the hand. Such probes are suitable for deriving measurements from more extensive tissue regions of the body than the finger probes described earlier, while still conferring the basic advantages of the probe, namely the prevention of distal venous blood pooling, the unloading of wall tension from arterial blood vessels, and the inhibition of retrograde venous shock wave propagation to the actual measurement site.

FIGS. 7a and 8a illustrate a probe, therein generally designated 110, constituted of a single section dimensioned for receiving the forearm and hand of the subject; FIG. 7b schematically illustrates a probe 120 constituted of two sections 121, 122, one dimensioned for receiving the hand and wrist of the subject, and the other part for receiving the forearm of the subject; and FIG. 7c schematically illustrates a probe 130 also constituted of two sections 131, 132, but in this case one section 131 is dimensioned for receiving the hand of the subject, while the other section 132 is dimensioned for receiving the wrist and forearm of the subject.

FIGS. 7e and 8e, respectively, illustrate three-section probes 140 and 150. The closed-end section 141, 151, preferably covers all the fingers of the hand, whereas the other two sections 142, 153 and 152, 153, respectively, may vary in dimension according to the particular application.

Figure 9:
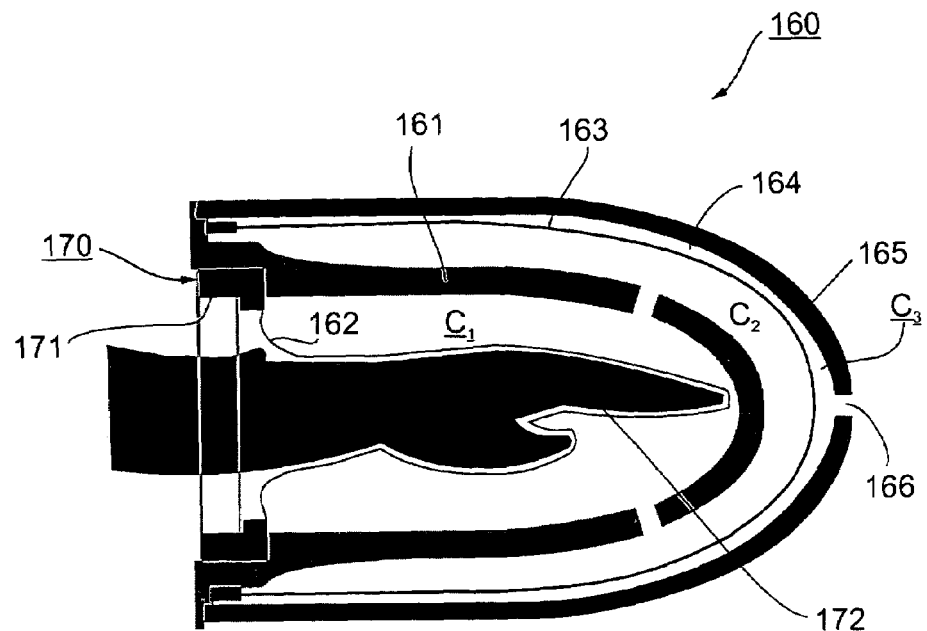
FIG. 9 is a cross-sectional view schematically illustrating a specific construction of the main part of a large-scale probe in accordance with FIGS. 7a-7e for receiving a subject's forearm.

The probes 110-150 schematically illustrated in FIGS. 7a-7e and 8a-8e, respectively, are of basically the same construction as in the above-identified U.S. patents and International Patent Applications (and in the other probes described herein), except that they would be designed and dimensioned for receiving a limb or part of a limb of the subject, rather than a finger of the subject. Further partitioning of the above described probes into additional sections is possible and may be useful due to the relatively large sample of tissue contained within the probe. Measurements of the pulsatile blood volume signals may be derived from any one or more of the sections illustrated in these probes, using any of the sensing modalities described. The fluid pressure applied to the various sections of the probe could be derived from fluid self-contained within the probe, or from fluid supplied from sources externally of the probe. Another possibility would be to use a fluid self-contained within the probe for applying the fluid pressure to the section at the closed end of the probe receiving the terminal-most part of the limb, and to utilize an external source of fluid for providing the pressure in one or more sections at the opposite open end of the probe receiving the more proximal regions of the limb. FIG. 9 illustrates, for purposes of example, such a large-scale probe for receiving the complete hand and wrist of the subject, wherein the pressure-producing fluid is self-contained within the probe itself as previously described. Such a probe may form part of an overall larger probe as illustrated in FIGS. 7a-7e and 8a-8e respectively. It may, for example, replace elements 121; 131; 141 and 142; or 151 and 152, of these figures, whereas the remainder of the large-scale probe may be of the externally pressurized type as described below with respect to FIG. 10.

The probe part illustrated in FIG. 9, and therein generally designated 160, also includes an inner casing 161 having an inner membrane 162 defining an inner chamber $C_1$; an outer membrane 163 defining a second chamber $C_2$ with casing 161 and communicating with chamber $C_1$ via openings 164 in the inner casing 161; and an outer casing 165 defining a third chamber $C_3$ with membrane 163, which chamber is vented to the atmosphere via a vent opening 166 formed in the outer casing 165. Probe 160 further includes a restraining member, generally designated 170, having an annular ring 171 adjacent to the open end of the probe, and a U-shaped arm 172 (or a pair of arms, corresponding to arm 72, 73 illustrated in FIG. 5) extending axially within the compartment receiving the subject's hand for restraining the membrane 162 from expelling the hand when chamber $C_1$ is pressurized. Probe 160 illustrated in FIG. 9 is otherwise constructed as described above, or in the above-identified U.S. patents and International Patent Applications, and is operative in the same manner as described therein for monitoring pulsatile blood volume changes, except that these changes are monitored in the complete hand of the subject, rather than merely in the distal portion of the subject's finger.

Figure 10:
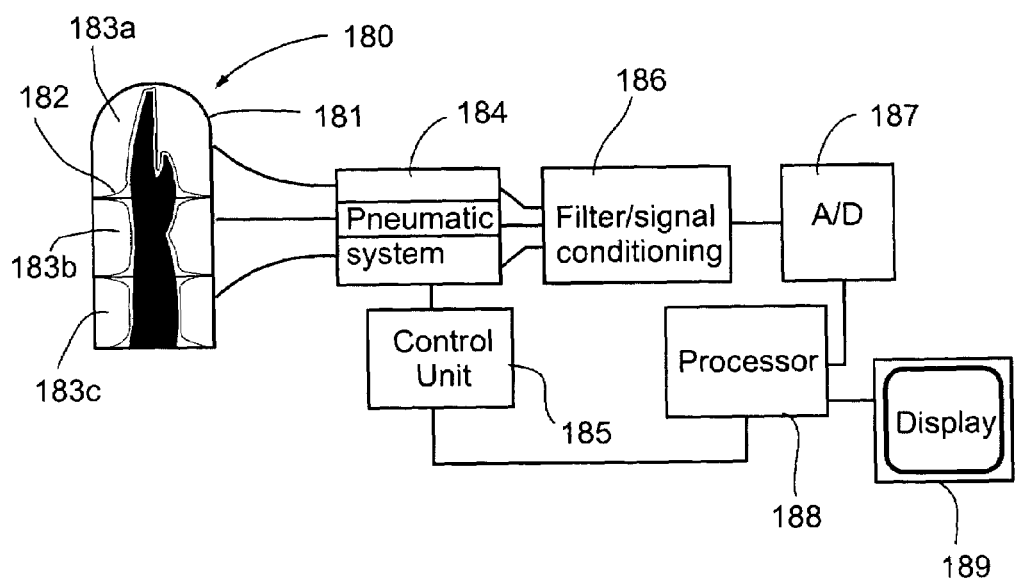
FIG. 10 schematically illustrates a large-scale probe in accordance with FIGS. 7b, 8b, but including an external fluid system, rather than an internal self-contained fluid system, for producing the predetermined static pressure applied to the body part (a limb or part of a limb) received within the probe.

FIG. 10 illustrates a three-section large-scale probe for receiving substantially the complete forearm of the subject. Thus, the large-scale probe illustrated in FIG. 10, and therein generally designated 180, includes a housing 181 having one or more inner membranes 182 engaged by restraining members, such as restraining member 20 and one or more annular rings 81 in FIG. 6, to define three inner chambers 183a, 183b, 183c, for applying predetermined static pressures to the portion of the forearm received in the respective section of the probe. In the probe illustrated in FIG. 10, the three chambers 183a-183c are supplied by fluid from an external fluid system, in this case a pneumatic system 184 under the control of a control unit 185. The pneumatic system 184 also outputs electrical signals to a filter/signal conditioning circuit 186 which signals, after conversion to digital form by an A/D converter 187, are processed within processor 188 which controls the control unit 185 and also produces a display in a display unit 189.

While FIG. 10 illustrates all three sections of the probe (i.e., containing the three inner chambers 183a-183c) as being pressurized from an external fluid system, it will be appreciated that the distal section of the probe (i.e., that containing the distal chamber 183a) could be pressurized by fluid from a self-contained source, as in FIG. 9; whereas the other two sections could be supplied with fluid from the external source.

An important advantage of the large-scale probe illustrated in FIGS. 7a-7e and 8a-8e, respectively, is that such a probe, particularly one including an external fluid system as shown in FIG. 10, is especially suited, to effect an induced ischemia test for detecting the presence of endothelial dysfunction in a patient, as described in the above-cited International Applications PCT IL00/00403 and PCT/IL01/00970. Such induced ischemia tests are typically applied on the brachial artery of the upper arm. In the conventional method for inducing ischemia, a blood pressure cuff is inflated to above systolic blood pressure on the upper arm. In the process of inflating the blood pressure cuff, a variable amount of blood may pass beyond the venous tourniquet formed by the upper arm blood pressure cuff when the cuff pressure is sub-systolic but above venous blood pressure. This effectively means that a degree of venous pooling may be induced distal to the occlusion cuff. This has the potential of inducing local reflex vascular effects, such as the veno-arteriolar reflex, which may distort the outcome of the test for endothelial dysfunction.

The large-scale probes as illustrated in FIGS. 7a-10 may be specifically designed to prevent the occurrence of such venous pooling in the entire measured vascular bed. Such probes would therefore confer substantial advantages for performing the induced ischemia test by controlling the applied pressure field over the entire tissue mass being studied.

When using a large-scale probe as illustrated in FIGS. 7a-10, it is also possible to apply supra-systolic external pressure to effectively empty all the blood vessels within the applied pressure field. That is, the ischemia would be induced by applying pressure to at least one of the plurality of sections of the compartment of the probe by fluid supplied from a fluid system external of the probe and of sufficient magnitude to occlude the flow of blood. The measurements of pulsatile volume changes taken during the application of counter-pressure for occluding blood flow can be used to ensure that a sufficient level of counter-pressure is being applied to completely occlude the flow of blood. The level of pressure can thus be regulated to the appropriate level if necessary. This would add a degree of certainty to the performance of the induced ischemia test.

An additional advantage in the use of such a large-scale probe is that it can allow simultaneous measurements of pulsatile blood volume changes in the distal ends of a plurality of fingers, thereby further increasing the amount of relevant data which can be derived from the measurements. The internal casing 161 and external casing 165 in the probe illustrated in FIG. 9, as well as the fore-arm probes illustrated in FIGS. 7a-7e, 8a-8e and 10, and the finger probes illustrated in FIGS. 1-5, may be rigid. However, they may also be semi-rigid, e.g., stiff but yielding, for patient comfort.

Figure 11:
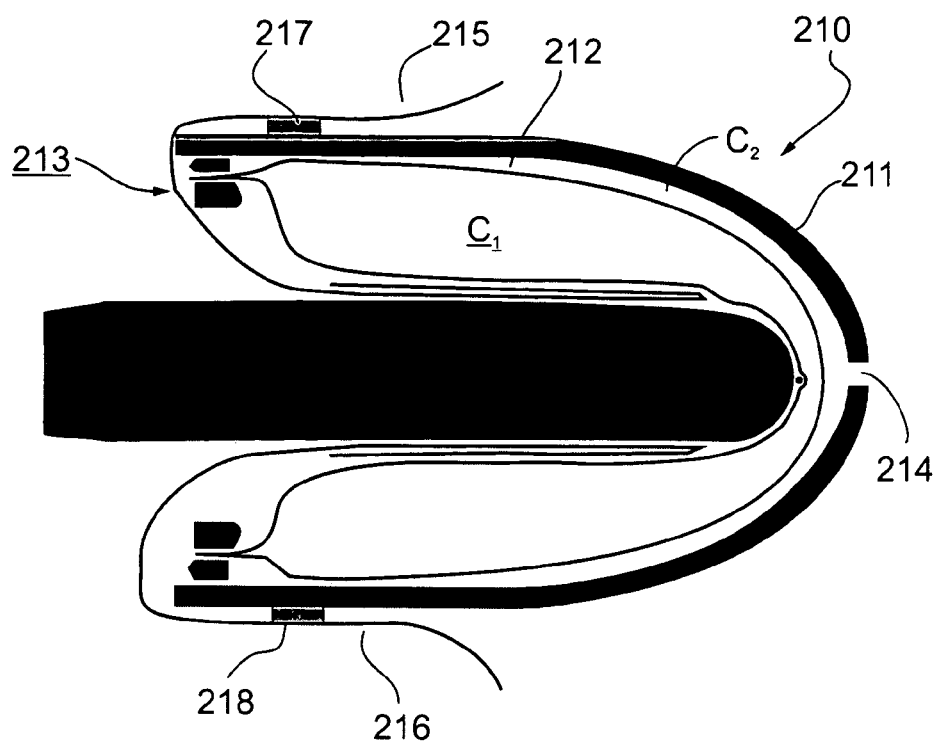
Figure 11A:
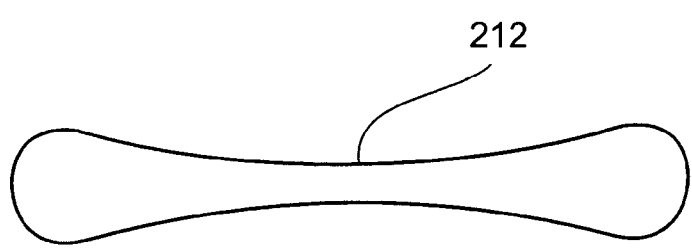
FIG. 11a illustrates the elastic bag in the probe of FIG. 11.
Figure 11B:
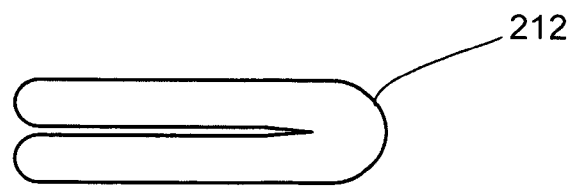
FIG. 11b illustrates the elastic bag of FIG. 11a in its folded condition.

FIG. 11 illustrates another probe, therein generally designated 210, constructed in accordance with the present invention, and FIGS. 11a-11d illustrate various components of the probe of FIG. 11. Probe 210 includes a thimble-shaped casing 211 open at one end and closed at its opposite end and receiving an elongated elastic bag 212 folded within casing 211 and retained therein by a retaining member 213. The elongated elastic bag 212 is more particularly illustrated in its unfolded form in FIG. 11a, and in its folded form in FIG. 11b. The interior of elastic bag 212 defines an inner chamber $C_1$, whereas the space between the surface of the elastic bag and the inner surface of casing 211 defines a second chamber $C_2$. Chamber $C_2$ is vented to the atmosphere by opening 214 in casing 211.

Retainer member 213 is more particularly illustrated in FIG. 11c, wherein it will be seen that it includes an annular ring 213a adjacent to the open end of the housing defined by casing 211, and a pair of arms 213b extending axially within the housing but terminating short of the close-end of the housing defined by casing 211. Restraining member 213 may be of the construction described above in FIG. 1, wherein the arms 213b are constituted of a U-shaped member; preferably, however, it is of the construction as described above with respect to FIGS. 5 and 6, wherein the arms 213b are two separate arms each terminating short of the closed end wall of the housing defined by casing 211. An external ring 214, shown in FIG. 11d, applied around the annular ring 213a of the restraining member 213, clamps the opposite ends of the folded elastic bag 212 to the annular ring 213e.

Probe 210 illustrated in FIG. 11 further includes removable liner strips 215, 216, corresponding to the removable liner strips 41, 42 in FIG. 1. These liner strips, which temporarily adhere to the outer surface of casing 211 by spots of adhesive 217, 218, facilitate the insertion of the subject's finger (or other body part) into the probe compartment, in the same manner as described above with respect to FIGS. 1 and 2a-2c.

Various types of sensors can be included within the probe, not only optical sensors as shown in FIGS. 1, 3 and, but also other types of sensor for measuring changes in the pulsatile blood volume and/or in the oxygen saturation level, as described above and/or in the above-identified U.S. patents and International Patent Applications.

The elastic bag 212 may be filled with a gas or liquid, or at least partially filled with a liquid. The advantage of using a liquid rather than a gas is that the diffusion rate through the walls of the elastic bag tends to be higher for gasses than for liquids, and therefore it would be possible to maintain a positive pressure within the bag for longer periods of time using a liquid.

It will thus be seen that an elongated elastic bag may be used in a probe having a self-contained fluid in the two chambers, corresponding to chambers $C_1$, $C_2$ in FIG. 1, which communicate with each other via an opening in the casing (e.g., openings 14 in casing 11, FIG. 1). When using such an inflatable elastic bag, it would be desirable to reduce diffusion of the self-contained fluid through the walls of the elastic bag in order to maintain a positive pressure within the bag for longer periods of time. In addition to using a liquid as at least a part of the fluid filling the bag as described above, other means may be used for reducing the diffusion rate through the walls of the elastic bag.

FIGS. 12a-12d illustrate the components of another probe construction utilizing an elongated elastic bag 220 for self-containing the fluid. One end 220a of elastic bag 220 is received over the outer surface of a rigid casing 221 (FIG. 12b), corresponding to casing 11 in FIG. 1, formed with a plurality of openings 222, corresponding to openings 14 in FIG. 1. To facilitate the application of end 220a of bag 220 around the outer surface of casing 221, the end 220a of the bag is formed with an opening, shown at 223 in FIG. 12a, which is sealed after that end of the bag has been applied over the casing 221, as shown at 223' in FIG. 12b.

The opposite end 220b of elastic bag 220 is then received within the casing 221 and is retained therein by retainer member 224. As shown in FIG. 12c, retainer member 224 includes an annular ring 224a and a U-shaped bar 224b, as described above with respect to FIG. 1, but may also be of the modified construction described above with respect to FIGS. 5a and 5b and 6.

When the elastic bag 220 and the retainer member 224 are assembled with respect to the casing 221, as illustrated in FIG. 12d, the bag may be inflated with the fluid, e.g., a gas or liquid, to produce the predetermined static pressure field to be applied to the subject's finger when received within the probe. After the bag is so inflated, it may be sealed. It will be appreciated that when the probe is so assembled, end 220b of the elastic bag 220 serves the equivalent of the inner membrane (12, FIG. 1) defining the inner chamber $C_1$ with the inner surface of casing 221; and that end 220a of the elastic bag serves as the second membrane (corresponding to 13, FIG. 1) which cooperates with the outer surface of the casing 221 to define the second chamber $C_2$ communicating with the first chamber $C_1$ via the openings 222 in the casing 221. It will also be appreciated that the retainer member 224 retains end 220b of bag 220 within the probe and defines the compartment therein for receiving the subject's finger to be monitored.

For the sake of simplifying the drawings, FIG. 12d does not illustrate the sensor or sensors (corresponding to sensor 30, FIG. 1) within the probe, the liner strips to facilitate insertion of the subject's finger into the probe, or the outer casing corresponding to casing 15 in FIG. 1.

The elongated elastic bag 220 is constructed and dimensioned such that, when its end 220a is applied around the outer surface of the casing 221, that end of the elastic bag is pre-tensioned. Pre-tensioning this end of the elastic bag reduces the diffusion rate of the fluid through the walls of the bag, and thereby enables a positive fluid pressure to be retained within the bag for longer periods of time. Such a construction also allows a larger volume of fluid to be retained at an effective zero pressure since any residual stretched wall tension at end 220a of the bag is unloaded when it collapses to the point of coming to rest on the outer wall of casing 221 and the effective probe pressure is zero.

FIG. 13 illustrates a self-contained fluid type probe, generally designated 310, also including an elongated elastic bag 320 applied over a rigid casing 321 as described above to define the outer membrane by one end 320a of the bag, and the inner membrane by the opposite end 320b of the bag, with the latter end being retained in place by retainer member 324, as described above. FIG. 13, however, also illustrates the outer casing 315, the sensor light source 331 and light detector 332 within the probe, and the removable liners 341, 342, corresponding to elements 15, 30, 41 and 42, respectively in FIG. 1.

FIG. 13, however, further illustrates the provision of a supporting medium within the inner chamber defined by end 320b of the elastic bag 320. This supporting medium is shown in FIG. 13 as being in the form of sponge-rubber inserts 350. These inserts should be of sufficient mechanical strength to support the end 320b of the elastic bag 320, serving as the inner membrane defining the inner chamber $C_1$ with the inner surface of the casing 321, and should be of sufficient volume so as to partially fill this chamber such that the added volume of the subject's finger, when received within the probe, produces the predetermined static pressure to be applied to the subject's finger. Thus, the volume of the fluid (e.g., gas) initially included within the chamber $C_1$ can be significantly reduced, thereby reducing the pressure within the chamber before the subject's finger is inserted into the probe. Such an arrangement is therefore also effective to reduce the diffusion rate of the fluid when the probe is not in use, and thereby maintains the pressure within the probe for longer periods of time.

The supporting medium partially filling the chamber may be of material other than sponge rubber, such as a low-density collapsible foam-like matrix which partially fills the chamber with a minimum effect on the deform ability of the membrane by the pulsatile blood volume changes in the subject's finger when received within the probe.

Figures 14A, 15A:
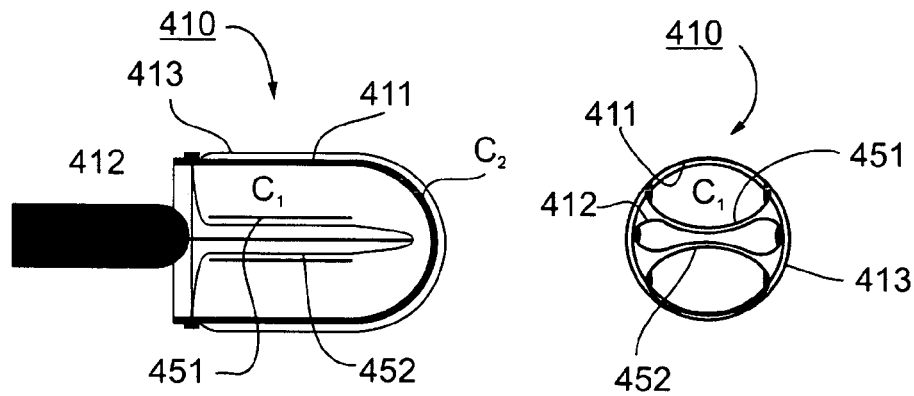
FIGS. 14a-14c and FIGS. 15a-15c schematically illustrate a bistable supporting member for supporting the membrane in a manner to minimize diffusion when the subject's finger is not received with the probe.
Figures 14B, 15B:
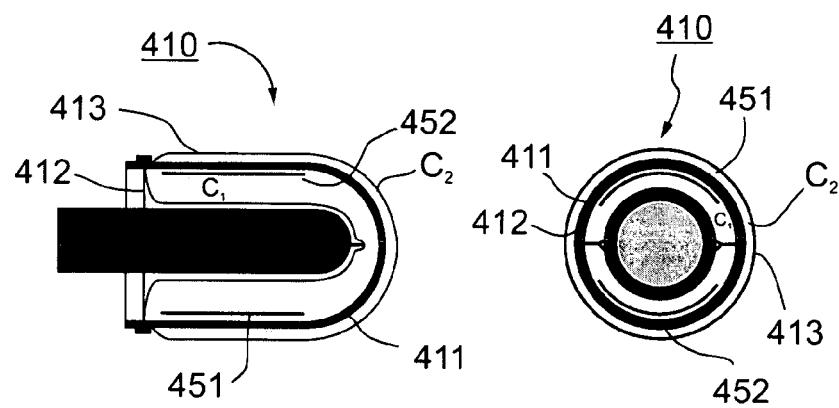
Figures 14C, 15C:
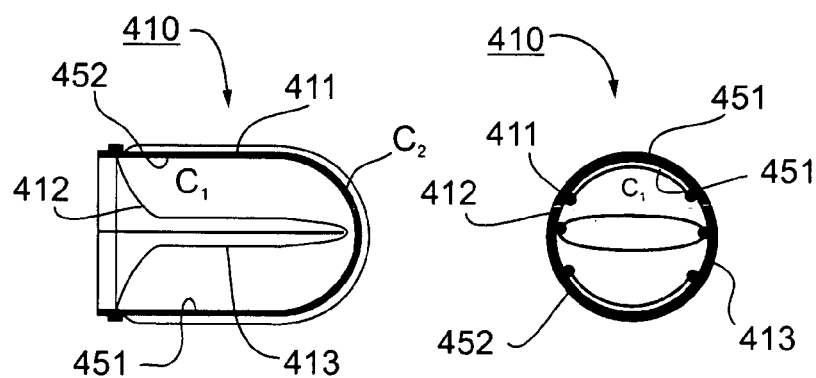

FIGS. 14a-14c are side views, and FIGS. 15a-15c are end views, schematically illustrating another manner, useful in a self-contained fluid type probe, for reducing the diffusion rate of the fluid when the probe is not in use. This technique is based on pre-tensioning the membrane prior to its use so as to prevent it from compressing the contained fluid, thereby reducing the effective pressure within the probe. This reduces the diffusion rate through the membrane when the probe is not in use.

The probe schematically illustrated in FIGS. 14a-15c, and therein designated 410, also includes a casing 411 having an inner membrane 412 defining an inner chamber $C_1$ within it, and an outer membrane 413 defining an outer chamber $C_2$ (best seen in FIGS. 14b and 15b) with the outer surface of the casing, with the two chambers in communication with each other via openings (not shown, but corresponding to openings 14 in FIG. 1).

Such a probe may also include a restraining member, a sensor, and the other elements of the probe as illustrated in FIG. 1 but not shown in FIGS. 14a-15c for purposes of simplifying the drawings.

In order to reduce the diffusion rate of the fluid within the two chambers $C_1$, $C_2$, the probe is provided with a pair of bistable elastic spring leaves 451, 452, carried by casing 441 and disposed within the inner chamber $C_1$ on opposite sides of that chamber. Each of the bistable elastic spring leaves 451, 452 is movable to a first stable position, as shown in FIGS. 14a and 15a, projecting away from the inner surface of the casing 441, or to a second stable position, as shown in FIGS. 14b and 15b, in contact with the inner surface of the casing 411. Thus, when the bistable elastic elements 451, 452 are in their inner positions shown in FIGS. 14a and 15a, they tend to expand chamber $C_1$ and thereby pre-tension the membranes, reducing the diffusion rate through the membranes, when the probe is not in use.

When the probe is to be used, the bistable elastic spring leaves 451, 452 are snapped to their outer positions, shown in FIGS. 14b and 15b, into engagement with the inner surface of the casing 411. This allows the user to insert a finger into the probe which displaces fluid from chamber $C_1$ and expands chamber $C_2$ to produce the predetermined static pressure in chamber $C_1$ applied to the finger.

After the probe has been used, the user may remove the finger and leave the bistable elastic spring leaves in their outer positions, as shown in FIGS. 14c and 15c, wherein they pre-tension the membrane, and thereby reduce the diffusion rate on the fluid. If the probe is not to be used again within a short period of time, the bistable elastic spring leaves 451, 452 may be snapped to their inner positions, as shown in FIGS. 14a, 15a.

While the invention has been described with respect to several preferred embodiments, it will be appreciated that these are set forth merely for purposes of example, and that many other variations, modifications and applications of the invention may be made.

What is claimed is:

1. A non-invasive probe for application to a body part of a subject for the detection of a medical condition of the subject, comprising:
    a housing defining a compartment closed at one end and open at the opposite end for receiving the subject's body part;
    a sensor for sensing a predetermined condition of said body part after being received within said compartment;
    and two removable liners of a low-friction sheet material lining two inner surfaces of said housing to face opposite sides of the body part when received in said compartment, each of said liners including an internal portion located within said housing, and an external portion extending externally of said housing to facilitate the slidable withdrawal of each liner from the housing after the body part has been inserted into said compartment.

2. The probe according to claim 1, wherein said internal portion of each liner located within said housing is folded upon itself to facilitate the slidable withdrawal of the liner from the housing after the body part has been inserted into said compartment.

3. The probe according to claim 1, wherein said external portion of each liner is temporarily adherent to the outer surface of said housing.

4. The probe according to claim 1, wherein said housing includes a casing and an inner membrane within said casing and defining an inner chamber for receiving a fluid to apply a predetermined static pressure to said body part when received within said compartment; and wherein said liner lines the inner surface of said inner membrane to facilitate the insertion of said body part into said compartment.

5. The probe according to claim 4, wherein said housing is configured and dimensioned for receiving the distal end of the subject's body part, including its terminal-most extremity; and wherein said housing further includes a restraining member located within said compartment to restrain said membrane from expelling the body part from said compartment when the chamber is pressurized by said fluid;
    said restraining member including an annular ring facing the open end of the housing, and a plurality of circumferentially-spaced arms extending axially within the compartment.

6. The probe according to claim 5, wherein there are two of said arms, said two arms being joined together in a U-shaped bend at their end adjacent the closed end of the housing.

7. The probe according to claim 5, wherein said arms terminate short of said closed end of the housing, and thereby short of said terminal-most extremity of the body part when received within said compartment.

8. The probe according to claim 5, wherein said annular ring is located adjacent to the open end of said housing.

9. The probe according to claim 5, wherein said annular ring is located inwardly of the open end of the housing to define, with an inner section of said inner membrane, an inner section of said compartment for receiving said body part; said inner membrane including an outer section defining an outer section of said compartment for receiving said body part, and an outer section of said inner chamber for applying said static pressure to said body part when received in said compartment.

10. The probe according to claim 5, wherein said arms of the restraining member mount said sensor within said compartment, and connections to the sensor from locations externally of the compartment.

11. The probe according to claim 10, wherein said sensor is an optical sensor and includes a light source and a light detector located externally of said compartment; and wherein said connections mounted on the arms of said restraining member include light guides for guiding light into the interior of the compartment from said light source located externally of the compartment and for guiding light from the interior of the compartment to said light detector located externally of the compartment.

12. The probe according to claim 5, wherein said housing also includes a transmitter for transmitting in a wireless manner data sensed by said sensor to a receiver externally of said compartment.

13. The probe according to claim 5, wherein said inner membrane is part of an inflatable elastic bag located within said housing and engaged by said restraining member to define said compartment for receiving the body part of the subject, said casing including an opening for venting to the atmosphere the space between said elastic bag and the inner face of said casing.

14. The probe according to claim 13, wherein said inflatable bag is of an elongated configuration, having a length many times its diameter, and is engaged in a folded condition by said restraining member to define said compartment.

15. The probe according to claim 13, wherein said inflatable bag is filled with a gas.

16. The probe according to claim 13, wherein said inflatable bag is at least partially filled with a liquid.

17. The probe according to claim 5, wherein said housing further includes an outer membrane over the outer surface of said casing and defining thereforth an outer chamber communicating with said inner chamber via an opening in said casing.

18. The probe according to claim 17, wherein said housing further includes an outer casing facing the outer surface of said outer membrane and defining therewith a third chamber; and wherein said outer casing includes a vent opening venting said third chamber to the atmosphere.

19. The probe according to claim 18, wherein said probe further includes a pressure transducer communicating with an opening in said outer casing for monitoring pressure changes within said third chamber.

20. The probe according to claim 17, wherein said inner membrane and said outer membrane are parts of an inflatable elongated elastic bag; one end of said elongated elastic bag being received over the outer surface of said casing to constitute said outer membrane defining said outer chamber; the opposite end of said elongated elastic bag being received within said casing to constitute said inner membrane engageable by said restraining member and defining said inner chamber communicating with said outer chamber via an opening in said casing.

21. The probe according to claim 20, wherein said casing and elongated elastic bag are so dimensioned that said one end of the elongated elastic bag, when received over said casing to define said outer chamber, is pre-tensioned sufficient to reduce diffusion of the fluid through the elastic bag by said static pressure when the body part is not received within the compartment, but not to substantially affect the deform ability of said inner membrane by pulsatile volume changes in the body part when received in said compartment.

22. The probe according to claim 20, wherein said inner chamber is partially filled with a supporting medium, and is at a fluid pressure below said predetermined static pressure, such that the added volume of the distal end of the subject's body part, when received within said compartment, produces said predetermined static pressure applied to said body part.

23. The probe according to claim 22, wherein said supporting medium includes a spongy body.

24. The probe according to claim 20, wherein the probe includes a pair of bistable elastic spring leaves carried by said casing and disposed within said inner chamber on opposite sides thereof; each of said bistable elastic spring leaves being movable to a first stable position projecting away from said casing inner surface into said inner chamber for pre-tensioning said membranes to reduce diffusion of the fluid through the membranes by the fluid pressure within said elongated elastic bag; each of said bistable elastic spring leaves being movable to a second stable position in contact with said casing inner surface to accommodate the subject's body part when introduced into said compartment.

25. The probe according to claim 1, wherein said housing includes a plurality of optical sensors for sensing optical properties of different portions of the body part received in said compartment.

26. The probe according to claim 1, wherein said housing further includes a movement detector for detecting movement of said body part.

27. The probe according to claim 1, wherein said housing is constructed and dimensioned to define a compartment for receiving the distal end, including the terminal-most extremity, of a digit of the subject.

28. The probe according to claim 1, wherein said housing is constructed and dimensioned to define a compartment for receiving the distal end, including the terminal-most extremity, of a limb of the subject.

29. The probe according to claim 1, wherein said sensor senses pulsatile volume changes in said body part.

30. The probe according to claim 1, wherein said sensor senses oxygen saturation level changes in said body part.

* * * * *